United States Patent
Harada et al.

(10) Patent No.: US 7,932,493 B2
(45) Date of Patent: Apr. 26, 2011

(54) METHOD AND SYSTEM FOR OBSERVING A SPECIMEN USING A SCANNING ELECTRON MICROSCOPE

(75) Inventors: Minoru Harada, Fujisawa (JP); Ryo Nakagaki, Kawasaki (JP); Kenji Obara, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 123 days.

(21) Appl. No.: 12/153,333

(22) Filed: May 16, 2008

(65) Prior Publication Data
US 2009/0084953 A1 Apr. 2, 2009

(30) Foreign Application Priority Data

Sep. 28, 2007 (JP) ................. 2007-253037

(51) Int. Cl.
*G01N 23/22* (2006.01)
*G06K 9/00* (2006.01)
(52) U.S. Cl. ........ 250/306; 250/307; 250/310; 382/148; 382/149
(58) Field of Classification Search ............ 250/306, 250/307, 309–311, 492.1, 492.2, 492.3, 559.1, 250/559.4, 559.39, 559.42, 559.43; 382/141, 382/145, 148, 149, 151, 282, 291
See application file for complete search history.

(56) References Cited

U.S. PATENT DOCUMENTS

| | | | |
|---|---|---|---|
| 6,657,221 B2 * | 12/2003 | Nakagaki et al. | 250/559.4 |
| 7,432,503 B2 * | 10/2008 | Honda et al. | 250/310 |
| 7,485,858 B1 * | 2/2009 | Obara et al. | 250/306 |
| 7,598,490 B2 * | 10/2009 | Kurihara et al. | 250/307 |
| 7,598,491 B2 * | 10/2009 | Fukunishi et al. | 250/310 |
| 2005/0146714 A1 * | 7/2005 | Kitamura et al. | 356/237.2 |
| 2006/0151700 A1 * | 7/2006 | Honda et al. | 250/310 |
| 2006/0289752 A1 * | 12/2006 | Fukunishi et al. | 250/310 |
| 2007/0031026 A1 * | 2/2007 | Kurihara et al. | 382/149 |
| 2009/0084953 A1 * | 4/2009 | Harada et al. | 250/307 |
| 2009/0121152 A1 * | 5/2009 | Obara et al. | 250/442.11 |

FOREIGN PATENT DOCUMENTS

| | | |
|---|---|---|
| JP | 2001-331784 | 11/2001 |
| JP | 2003-98114 | 4/2003 |
| JP | 2005-285746 | 10/2005 |
| JP | 2007-40910 | 2/2007 |

* cited by examiner

*Primary Examiner* — Bernard E Souw
(74) *Attorney, Agent, or Firm* — Antonelli, Terry, Stout & Kraus, LLP.

(57) ABSTRACT

It is intended to reduce the auto focusing time and to increase the stability in a case that a defect on a specimen that has been detected by an inspection apparatus is observed by using a scanning electron microscope. One or more regions to be used for auto focusing are set in an imaging region or its neighborhood on the basis of semiconductor design information. A target focusing position in the imaging region is determined by performing auto focusing using the thus-set regions. The determined target focusing position is used for low-magnification imaging and high-magnification imaging. An auto focusing mode that is suitable for each imaging region is selected on the basis of the semiconductor design information.

14 Claims, 9 Drawing Sheets

FIG.3
(a)
(b)
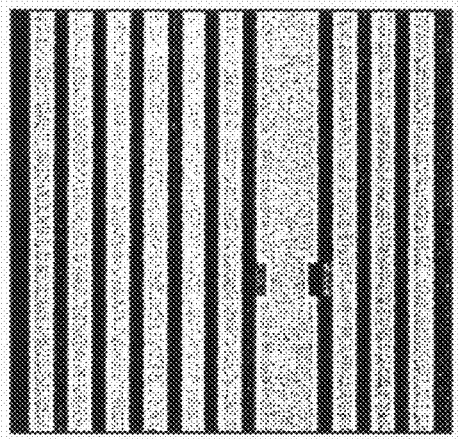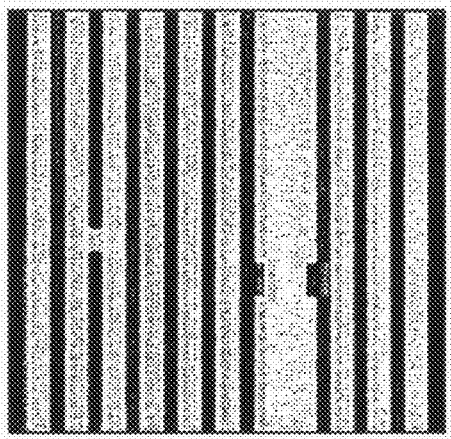
(c)
(d)
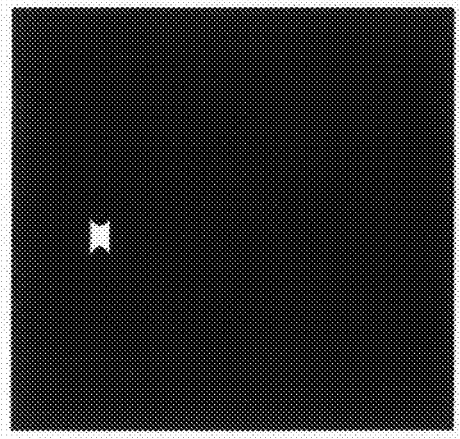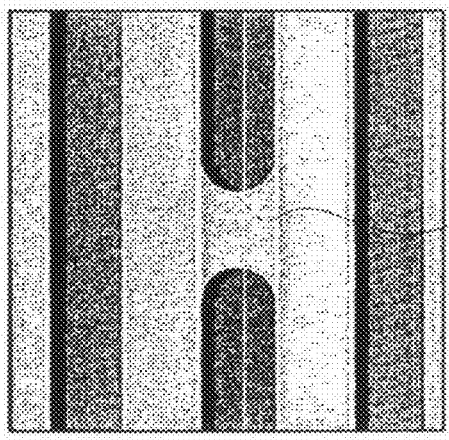

METHOD AND SYSTEM FOR OBSERVING A SPECIMEN USING A SCANNING ELECTRON MICROSCOPE

CLAIM OF PRIORITY

The present application claims priority from Japanese application serial no. P2007-253037, filed on Sep. 28, 2007, the content of which is hereby incorporated by reference into this application.

BACKGROUND OF THE INVENTION

The present invention relates to a method and system for observing a specimen using a scanning electron microscope which serve to observe defects etc. occurring in a manufacturing process of a semiconductor wafer, a liquid crystal panel, or the like.

To increase the production yield of a semiconductor, early determination of a cause of occurrence of defects in a manufacturing process is important. At present, in semiconductor manufacturing places, defects are analyzed by using a defect inspection apparatus and an observing apparatus. The defect inspection apparatus is an apparatus which observes a wafer using an optical means or an electron beam and outputs detected defect coordinates.

It is important for the defect inspection apparatus to process a wide area at high speed. Therefore, in the defect inspection apparatus, the amount of image data is reduced by setting the pixel size (dimensions on a specimen that is detected by one pixel of a detector) of an image to be acquired as large (low in resolution) as possible. In many cases, even if presence of a defect is recognized from a detected low-resolution image, a detailed type of the defect cannot be determined. This is the reason why the observing apparatus is used. The observing apparatus is an apparatus which images a defect coordinates position on a wafer at a high resolution using an output of the defect inspection apparatus and outputs a resulting image.

To observe a defect in detail, a resolution on the order of several nanometers is necessary partly because the degree of miniaturization has increased in semiconductor manufacturing processes and accordingly defect sizes have decreased to of the order of tens of nanometers. Therefore, in recent years, observing apparatus (hereinafter referred to as review SEMs) using a scanning electron microscope (SEM) have come to be used widely. In semiconductor mass-production lines, observation work is desired to be automated. And review SEMs incorporate an ADR (automatic defect review) function of automatically collecting images of defect coordinates positions on a wafer and an ADC (automatic defect classification) function of automatically classifying the acquired images.

The depth of focus of scanning electron microscopes is about 0.5 to 1.0 μm. Therefore, to take an unblurred image, it is necessary to set the focusing position of an electron beam at a target focusing position. The term "target focusing position" means a focusing position that is located at a subject surface of a specimen and hence enables taking of an unblurred image. In general, a specimen has a variation in height and hence individual observation regions have different target focusing positions.

Auto focus is a function of automatically calculating a target focusing position of an observation region. One auto focus technique is such that plural images are taken while the focusing position is varied, a focus measure indicating the degree of focusing is calculated from each image, and a focusing position that provides a maximum focus measure is determined as a target focusing position. In an image that is taken with the focusing position set at a target focusing position, the density value of an edge portion varies steeply. On the other hand, in an image that is taken with the focusing position deviated from a target focusing position, the density value of an edge portion varies gently. In view of this, the steepness of a density variation of an edge portion (hereinafter referred to as "edge steepness") in an image taken is used as a focus measure. Therefore, in auto focusing using a SEM image, it is necessary that an image taken include high-contrast edges. This technique is effective also in SEMs and is also used in review SEMs.

In semiconductor mass-production lines, it is necessary to correctly monitor how defects are occurring in a manufacturing process. To this end, it is necessary that as many wafers as possible be subjected to inspection by an inspection apparatus and observation and classification of defects by a review SEM. In the inspection apparatus and the review SEM, increase in processing speed (i.e., throughput) is particularly important. Conventional techniques relating to such a review SEM are disclosed in JP-A-2001-331784. This reference discloses a configuration of a review SEM, ADR and ADC functions and operation sequences, a method for displaying acquired images and a classification result, and other things.

Performing auto focusing in acquiring a SEM image is disclosed in JP-A-2005-285746.

JP-A-2003-98114 discloses an ADR sequence for determining a defect position without using a reference image by utilizing the periodicity of patterns in an imaging region of a memory cell area.

Furthermore, JP-A-2007-40910 discloses an ADR sequence for determining a defect position without using a reference image even in the case where an imaging region includes part of logic patterns that exist in a peripheral portion of a memory cell area.

FIG. 2 shows a conventional ADR sequence. In general, errors of defect coordinates that are output from a defect inspection apparatus with respect to actual defect coordinates have variations of about ±4 μm. Therefore, when a region that has a field of view of about 2.5 μm and should include defect coordinates that are output from a defect inspection apparatus is taken at a high magnification (e.g., 50,000), the defect may not be included in the field of view. This is avoided in the following manner. First, a region having a field of view of about 9 μm is imaged at a low magnification (e.g., 15,000) (hereinafter referred to as "low-magnification imaging"). Defect coordinates are determined from a resulting low-magnification image. Finally, a position corresponding to the determined defect coordinates is imaged at a high magnification (hereinafter referred to as "high-magnification imaging").

First, at step S201, to acquire a low-magnification reference image, a table that is mounted with a specimen is moved to a reference coordinates position. At step S203, a coordinates position that is free of a defect and has the same wiring patterns as a defect coordinates position is imaged at a low magnification (taking of a low-magnification reference image). At step S204, to acquire a low-magnification defect image, the stage is moved to the defect coordinates position. At step S206, the defect coordinates position is imaged at the same low magnification (taking of a low-magnification defect image). The reference image and the defect image are taken after calculating target focusing positions of the two imaging regions by auto focusing and setting the focusing position to the target focusing positions (S202 and S205), respectively. At step S207, defect coordinates are determined by taking a difference between the two images acquired.

In general, the depth of focus is shallower in high-magnification imaging than in low-magnification imaging. Therefore, a target focusing position needs to be determined with higher accuracy in high-magnification imaging. In SEM image auto focusing, when the depth of focus is great, it is difficult to determine a target focusing position accurately. Therefore, the accuracy of a target focusing position obtained by low-magnification SEM image auto focusing is insufficient for high-magnification imaging. In view of this, in high-magnification imaging, at step S209 SEM image auto focusing is performed again at a high magnification. As a result, the time taken by auto focusing accounts for a large part of the time taken by a defect review, which is a factor of throughput reduction.

In SEM image auto focusing, it is necessary to image a region where high-contrast edges exist (hereinafter referred to as "edge region") such as a region where wiring patterns are formed. In JP-A-2005-285746, the imaging time and the processing time are shortened by extracting a narrow region including edges from a low-magnification image and setting it as an imaging region of high-magnification SEM image auto focusing (hereinafter referred to as "auto focus execution region") (S208).

Where the technique disclosed in JP-A-2005-285746 is used in ADR for observing a defect detected by a separate inspection apparatus, since an auto focus execution region is set after low-magnification imaging, it is difficult to increase the processing speed of low-magnification SEM image auto focusing which is performed before the low-magnification imaging. That is, in the ADR sequence of the conventional method, since low-magnification imaging is performed in a state that an auto focus execution region has not been set yet, a target focusing position cannot be detected reliably by one auto focusing operation. There may occur a case that a region suitable for auto focusing needs to be found by repeating auto focusing. The time taken by low-magnification SEM image auto focusing accounts for a large part of the ADR processing time. It is therefore desired to shorten the processing time of low-magnification SEM image auto focusing.

In a region on a semiconductor wafer where no wiring patterns are formed, edges exist only in a defect. In such a case, it is difficult in terms of principle to determine a target focusing position with high reliability by low-magnification SEM image auto focusing because an imaged defect is small and hence a focus measure cannot be calculated stably. The conventional ADR sequence has a problem that it is unstable because a target focusing position is calculated by low-magnification SEM image auto focusing even in regions where no wiring patterns are formed.

SUMMARY OF THE INVENTION

The present invention provides a specimen observing method and apparatus using an electron microscope in which the above-described problems of the related art have been solved and the processing time of low-magnification SEM image auto focusing is shortened.

The invention also provides a specimen observing method and apparatus using an electron microscope in which the above-described problems of the related art have been solved and a target focusing position of low-magnification SEM image auto focusing can be determined stably even in a region on a specimen where no wiring patterns are formed.

More specifically, in the invention, a review SEM apparatus comprises means for setting a SEM auto focus execution region using semiconductor design information (hereinafter referred to as "design information") before low-magnification imaging, performing SEM image auto focusing at a high magnification, and performing low-magnification imaging and high-magnification imaging using a target focusing position acquired in the previous step, and means for making it possible to set a SEM image auto focus execution region without the need for aligning a design information coordinate system and an observation coordinate system with each other closely. This configuration makes it possible to shorten the processing time of auto focusing.

Furthermore, in the invention, a review SEM apparatus comprises means for selecting an auto focusing mode suitable for a region concerned on the basis of design information of a low-magnification imaging region and its neighborhood, means for setting plural regions to be used for auto focusing in the low-magnification imaging region or its neighborhood, and means for inferring a target focusing position of the imaging region from target focusing positions of the plural regions. This configuration makes it possible to determine an auto focus target focusing position stably in a low-magnification SEM image even for a region on a specimen where no wiring patterns are formed.

The invention makes it unnecessary to perform auto focusing for low-magnification imaging and thereby shorten the time required for observation of one defect. Furthermore, the invention can increase the stability of auto focusing by selecting a suitable auto focusing mode and using target focusing positions at plural locations.

These and other objects, features, and advantages of the invention will be apparent from the following more particular description of preferred embodiments of the invention, as illustrated in the accompanying drawings.

BRIEF DESCRIPTION OF THE DRAWINGS

FIG. 3(a) shows an example of low-magnification reference image that was taken by ADR;

FIG. 3(b) shows an example of low-magnification defect image that was taken by the ADR;

FIG. 3(c) shows a difference image between the low-magnification reference image of FIG. 3(a) and the low-magnification defect image of FIG. 3(b);

FIG. 3(d) shows an image taken by imaging, at a high magnification, a defect position 301 that was determined from FIG. 3(c);

DESCRIPTION OF THE PREFERRED EMBODIMENTS

A defect observing apparatus (review SEM) using a scanning electron microscope according to the present invention will be hereinafter described.

Embodiment 1

Figure 1:
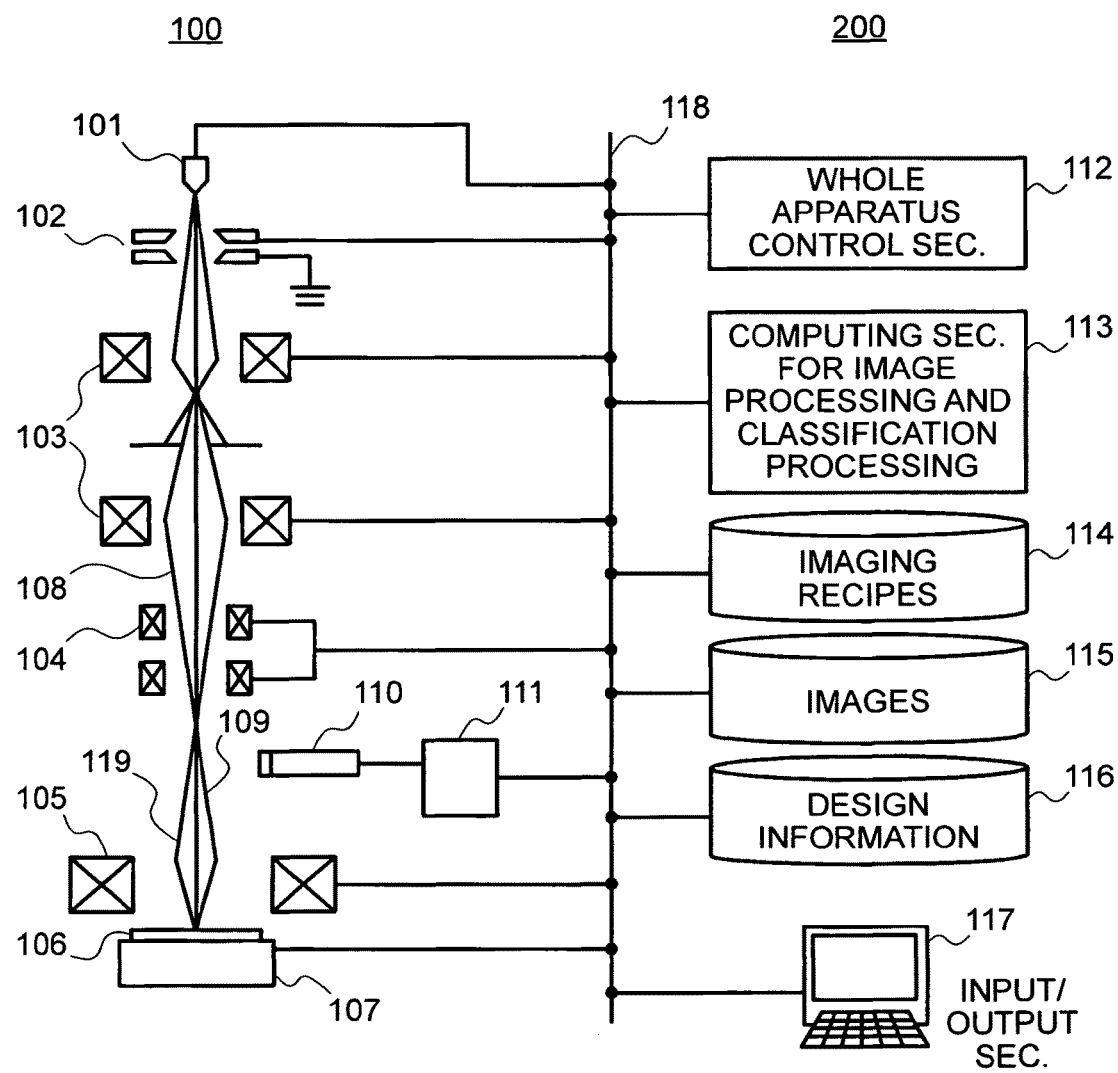
FIG. 1 is a block diagram showing the entire configuration of an apparatus according to the invention.
Figure 2:
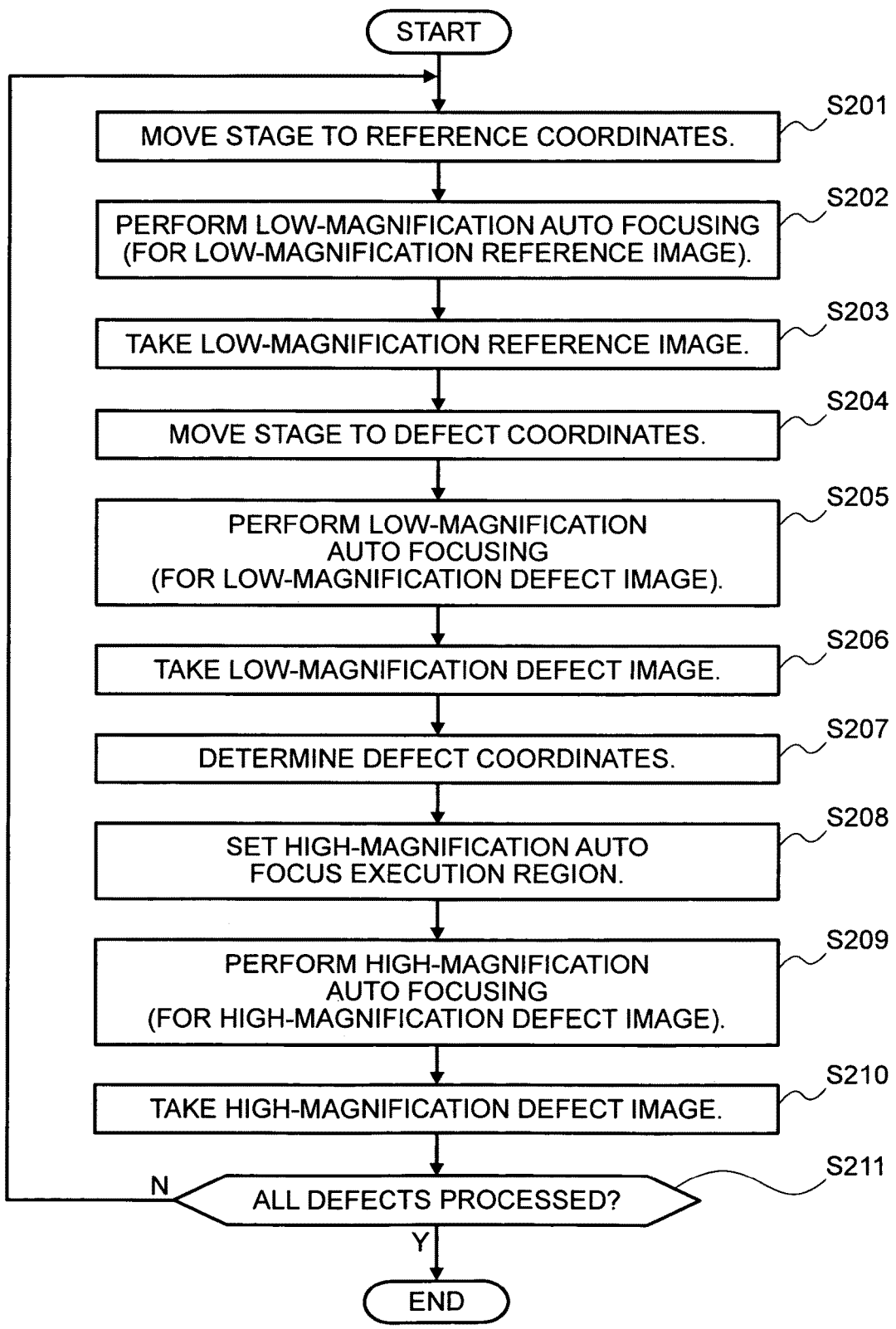
FIG. 2 is a flowchart of a conventional ADR sequence.

FIG. 1 shows the apparatus configuration of a review SEM according to the invention. The review SEM apparatus according to the invention is mainly composed of a SEM image acquiring unit 100 and a signal processing unit 200 which are connected to each other by a bus 118. In the SEM image acquiring unit 100, reference numeral 101 denotes an electron source for generating primary electrons 108; 102, acceleration electrodes for accelerating the primary electrons 108; 103, a focusing lens for focusing the primary electrons 108; 104, a deflector for deflecting the primary electrons 108 for a two-dimensional scan; and 105, an objective lens for focusing the primary electrons 108 on a specimen 106. Reference numeral 107 denotes a stage which can be moved in the XY plane with the specimen 106 mounted thereon. Reference numeral 110 denotes a detector for detecting secondary electrons 109 generated from the specimen 106. Reference numeral 111 denotes a digitizing means for digitizing (A/D-converting) a detected signal. These components are connected to a whole apparatus control section 112 via the bus 118.

On the other hand, the signal processing unit 200 is equipped with a computing section 113 for performing image processing and classification processing on an acquired image, a storage section 114 for storing, for example, observation condition information (recipes) including coordinates information, obtained through inspection by a separate defect inspection apparatus, of defects as subjects of automatic observation among defects detected by inspecting the specimen 106 with the defect inspection apparatus, a storage section 115 for storing image data, a storage section 116 for storing semiconductor design information, and input/output section 117 consisting of such devices as a keyboard and a mouse for giving instructions to the apparatus and a monitor and a printer for outputting data from the apparatus. These components are connected to each other by the bus 118.

Next, an ADR sequence of the review SEM according to the invention will be described with reference to FIG. 4. First, before imaging, a wafer specimen 106 is placed on the stage 107. An operator selects, through the input/output section 117, a recipe to be used for measurement from the plural recipes registered in the storage section 114 and instructs the whole apparatus control section 112 to perform ADR and ADC under the conditions of the selected recipe. It is assumed that each recipe contains various electron optics system conditions (e.g. an acceleration voltage, a probe current, and imaging magnification) etc. for imaging. Then, the whole apparatus control section 112 reads coordinates information of defects as subjects of automatic observation from the storage section 114. Defect images are collected by executing steps S401-S408 (described below) by using the read-in pieces of coordinates information of the respective defects.

Before describing the sequence, a defect coordinates determining method in ADR will be described with reference to FIGS. 3(a)-3(d). In the ADR, a defect position is determined in an observation field of view of the review SEM by using defect coordinates information that was detected in advance through inspection by a separate defect inspection apparatus and that has been read from the storage section 114.

A defect position is determined by calculating a difference between a low-magnification defect image taken by imaging, at a low magnification, a region including the defect coordinates position and a low-magnification reference image taken by imaging, at a low magnification, a region including a coordinates position that has the same wiring patterns as the defect coordinates position but is free of the defect.

Plural chips in which the same circuit pattern is formed are arranged on a semiconductor wafer. Usually, a low-magnification reference image is taken by imaging a region, including a position corresponding to the defect coordinates position, in a chip that is adjacent to the chip where the defect exists. FIGS. 3(a) and 3(b) show an example of low-magnification reference image and an example of low-magnification defect image, respectively. FIG. 3(c) shows a difference image between the images of FIGS. 3(a) and 3(b); a defect position (a white portion in the black background) is made visible in FIG. 3(c). FIG. 3(d) shows an image taken by imaging, at a high magnification, a defect position 301 that was determined from FIG. 3(c).

Returning to FIG. 4, steps S401-S406 will be described below. At step S401, to take a low-magnification reference image using coordinates information of an observation subject defect read from the storage section 114, the stage 107 is moved so that an electron beam can strike an imaging region, corresponding to the defect coordinates position, of an adjacent chip. At step S402, before taking a low-magnification reference image, an electron beam target focusing position of the imaging region of the image concerned is calculated by auto focusing (e.g., a method as described in the background section in which focus measures are calculated from plural images taken while the focusing position is varied gradually and sequentially and a position that provides a maximum focus measure is employed as a target focusing position; this method will be described later in detail with reference to FIG. 8) and resulting target focusing position information is stored in a storage section 410. At step S403, the target focusing position information is read from the storage section 410, the focusing position is set to the target focusing position, and a low-magnification reference image is taken.

Then, a low-magnification defect image is taken at steps S404-S406. First, at step S404, as in the case of taking a low-magnification reference image, the stage 107 is moved by using the coordinates information of the observation subject defect that is read from the storage section 114. At step S405, auto focusing is performed by the same method as employed at step S402, whereby a target focusing position of the defect coordinates region as an imaging subject is calculated. The calculated target focusing position information is stored in a storage section 411. At step S406, the target focusing position is read from the storage section 411, the focusing position is set to the target focusing position, and a low-magnification defect image is taken. The storage sections 410 and 411 may be the storage section 114 which stores imaging recipes.

Each of a low-magnification image and a high-magnification image are taken according to the following procedure. First, primary electrons 108 emitted from the electron source 101 are accelerated by the acceleration electrodes 102, focused by the focusing lens 103 and then by the objective lens 105, and applied to a measurement portion of the specimen 106. The deflector 104 deflects the primary electron beam so that a field-of-view range that is determined by a magnification factor registered in a recipe is scanned with the primary electrons 108 two-dimensionally. Secondary electrons 109 etc. that are generated from the specimen surface being irradiated with the electron beam are captured by the detector 110 and converted by a scintillator (not shown) into an optical signal, which is converted by a photo multiplier tube (not shown) into an electrical signal, which is converted (A/D-converted) into a digital signal by the digitizing means 111. The thus-obtained digital signal is stored in the storage section 115 as a digital image.

Returning to FIG. 4, steps S407 and S408 will be described below. At step S407 (defect extraction step), a portion where the low-magnification reference image taken at step S403 and the low-magnification defect image taken at step S406 are different from each other is determined by difference calculation processing (image processing) and a defect position in the image is determined on the basis of the position information of this difference-found portion. At step S408, a high-magnification defect image is taken by imaging a region having the extracted defect position as the center. This is done after reading the target focusing position from the storage section 411 and setting the focusing position to the target focusing position. FIG. 3(d) shows an example of high-magnification defect image that was taken in the above manner.

An image that enables detailed observation of one defect can be acquired by the above steps. In the ADR, the above steps are executed for all defect coordinates positions (S409).

The auto focusing steps S402 and S405 of the ADR sequence according to the embodiment will be described with reference to FIG. 5. First, at step 502, the whole apparatus control section 112 extracts, in an imaging region and its neighboring region, a region where pattern edges exist using design information read from the storage section 116 and sets an auto focus execution region. Since the information amount of the design information is large, design information of the observation subject and its neighborhood is cut out in advance at step S501, whereby the search range is narrowed and the processing speed is increased. In the following, the cut-out design information will be referred to as "neighborhood design information."

Conditions that should be satisfied by an auto focus execution region will be described here. In auto focusing which is performed in acquiring a SEM image, a target focusing position is inferred on the basis of the sharpness of a portion, corresponding to a pattern edge, of an image signal of patterns in a SEM image, that is, the edge sharpness. Therefore, a region including many high-contrast edges is desirable. In the review SEM according to the invention, the electron beam scanning interval can be changed. However, if the scanning interval is increased, high-frequency components in the scanning interval direction are lost. More specifically, when a SEM image of plural line patterns that are arranged on a specimen, if the scanning interval is increased in the case where an electron beam runs along the longitudinal direction of the line patterns, there may occur an event that edge portions of line patterns are located between electron beam scanning lines and signals corresponding to the pattern edge portions cannot be obtained.

As mentioned above, in the SEM image auto focusing, a focus measure is calculated on the basis of the edge sharpness (i.e., high-frequency components). Therefore, it is not preferable that high-frequency components are lost when the scanning interval is increased. In view of this, to avoid receiving influence of the scanning interval, the electron beam scanning direction is adjusted so as to be perpendicular to the pattern edge extending direction.

Figure 7:
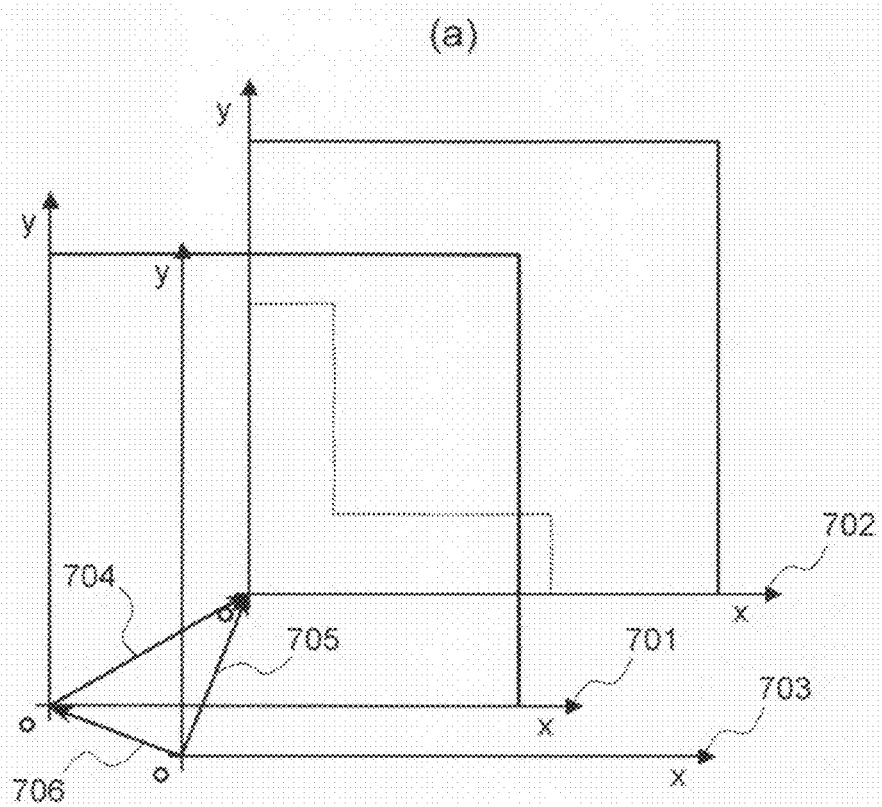
FIG. 7(a) shows a relationship between an observation coordinate system 701 and a design information coordinate system 702 in which reference numeral 704 denotes an example of error between them.
FIG. 7(b) shows design information, cut out of design information read from a storage section 116, of a region corresponding to a low-magnification image in a state that the error 704 shown in FIG. 7(a) exists.
FIG. 7(c) shows a low-magnification image that is taken by imaging a specimen actually with a SEM image acquiring unit in a state that the error 704 shown in FIG. 7(a) exists.

Before describing step S502 for setting an auto focus execution region on the basis of design information in the auto focusing according to the embodiment, an issue to be resolved will be described with reference to FIGS. 7(a)-7(d). FIG. 7(a) shows a relationship between an observation coordinate system 701 and a design information coordinate system 702. As in this example, an error 704 generally exists between the observation coordinate system 701 and the design information coordinate system 702. Causes of the error 704 are an error 705 occurring in setting a wafer coordinate system 703, a stage and beam application error 706 at the time of imaging, etc. In particular, the stage and beam application error 706 varies from one imaging operation to another. Therefore, it is difficult to make the observation coordinate system 701 and the design information coordinate system 702 coincide with each other. FIGS. 7(b) and 7(c) show design information 707, cut out of design information read from the storage section 116, of a region corresponding to a low-magnification image and a low-magnification image 708 that is taken by imaging a specimen actually with the SEM image acquiring unit 100, respectively, in a state that the error 704 shown in FIG. 7(a) exists.

If an auto focus execution region 710 is set on a wiring pattern 709 of the design information as shown in FIG. 7(b) in a state that the error 704 as shown in FIG. 7(a) exists between the observation coordinate system 701 and the design information coordinate system 702, there may occur an event that as shown in FIG. 7(c) a wiring pattern 712 does not overlap with an auto focus execution region 711 at the time of imaging and auto focusing fails. To solve this problem, it is necessary to take into consideration the error 704 between the observation coordinate system 701 and the design information coordinate system 702 in setting an auto focus execution region.

The procedure of the auto focus execution region setting step S502 will be described by using an example of wiring pattern shown in FIGS. 6(a)-6(d). First, line segments as edges are extracted from design information of a neighborhood design information region 601 which includes and is wider than a low-magnification imaging region 602 and regions where edges are concentrated (hereinafter referred to as "edge-concentrated regions") are generated by grouping edges whose inter-edge distances are smaller than a threshold value ThD for each of a set of horizontally extending edges and a set of vertically extending edges.

Figure 6:
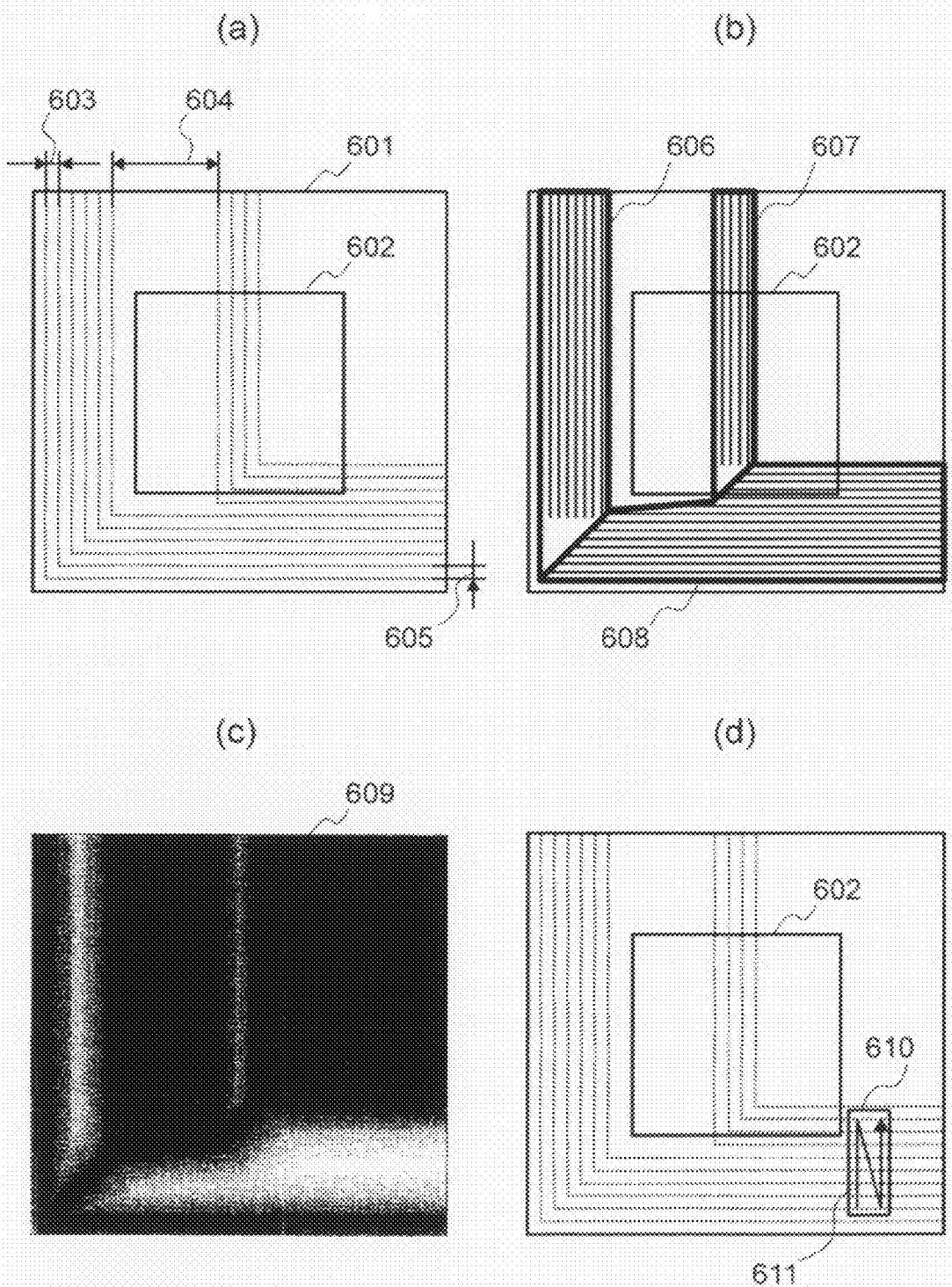
FIG. 6(a) shows a neighborhood design information region 601 in which an inter-edge distance 603 between vertically extending edges is not larger than a threshold value ThD, an inter-edge distance 604 between vertically extending edges is larger than the threshold value ThD, and an inter-edge distance 605 between horizontally extending edges is smaller than the threshold value ThD.
FIG. 6(b) shows a state that three edge-concentrated regions 606, 607, and 608 are generated.
FIG. 6(c) shows a distance map obtained by calculating a shortest distance between each coordinates position in each edge-concentrated region and its end lines in which the color is varied according to the distance from the end lines (the color comes closer to white as the distance increases)
FIG. 6(d) shows an example of auto focus execution region 610 set resultingly.

In the example of FIG. 6(a), as for the vertically extending edges, an inter-edge distance 603 is not larger than the threshold value ThD and an inter-edge distance 604 is larger than the threshold value ThD. Therefore, two edge-concentrated regions 606 and 607 are generated as shown in FIG. 6(b). As for the horizontally extending edges, an inter-edge distance 605 is smaller than the threshold value ThD and hence an edge-concentrated region 608 is generated as shown in FIG. 6(b). Usually, the threshold value ThD is set according to the size of the auto focus execution region.

Then, as shown in FIG. 6(c), a distance map 609 is generated by calculating a shortest distance between each coordinate position in each edge-concentrated region and the end lines of the region. In the distance map 609 of FIG. 6(c), the color is changed according to the distance from the end lines of each region; the color comes closer to white as the distance from the end lines of each region becomes longer. The distance map 609 represents the robustness against the error between the coordinate systems. That is, as the distance from the end lines of a region increases (i.e., as the color comes closer to white in the distance map of FIG. 6(c)), the probability increases that the edge overlaps with an auto focus execution region even if the error between the coordinate systems is large. Therefore, it is appropriate to set an auto focus execution region so in a region where the shortest distance from the end lines is longest in the distance map 609.

FIG. 6(d) shows an example of auto focus execution region 610 that is set in the above manner. In the auto focus execution region 610, an electron beam scanning direction 611 is set perpendicularly to the longitudinal direction of the wiring patterns, that is, the edge extending direction. Although the example of FIGS. 6(a)-6(d) include the horizontally extending edges and the vertically extending edges, the above processing can accommodate a case that edges extend in an oblique direction.

An auto focus execution region may be set from an image which is based on a digitized version of design information which is geometrical information.

Figure 4:
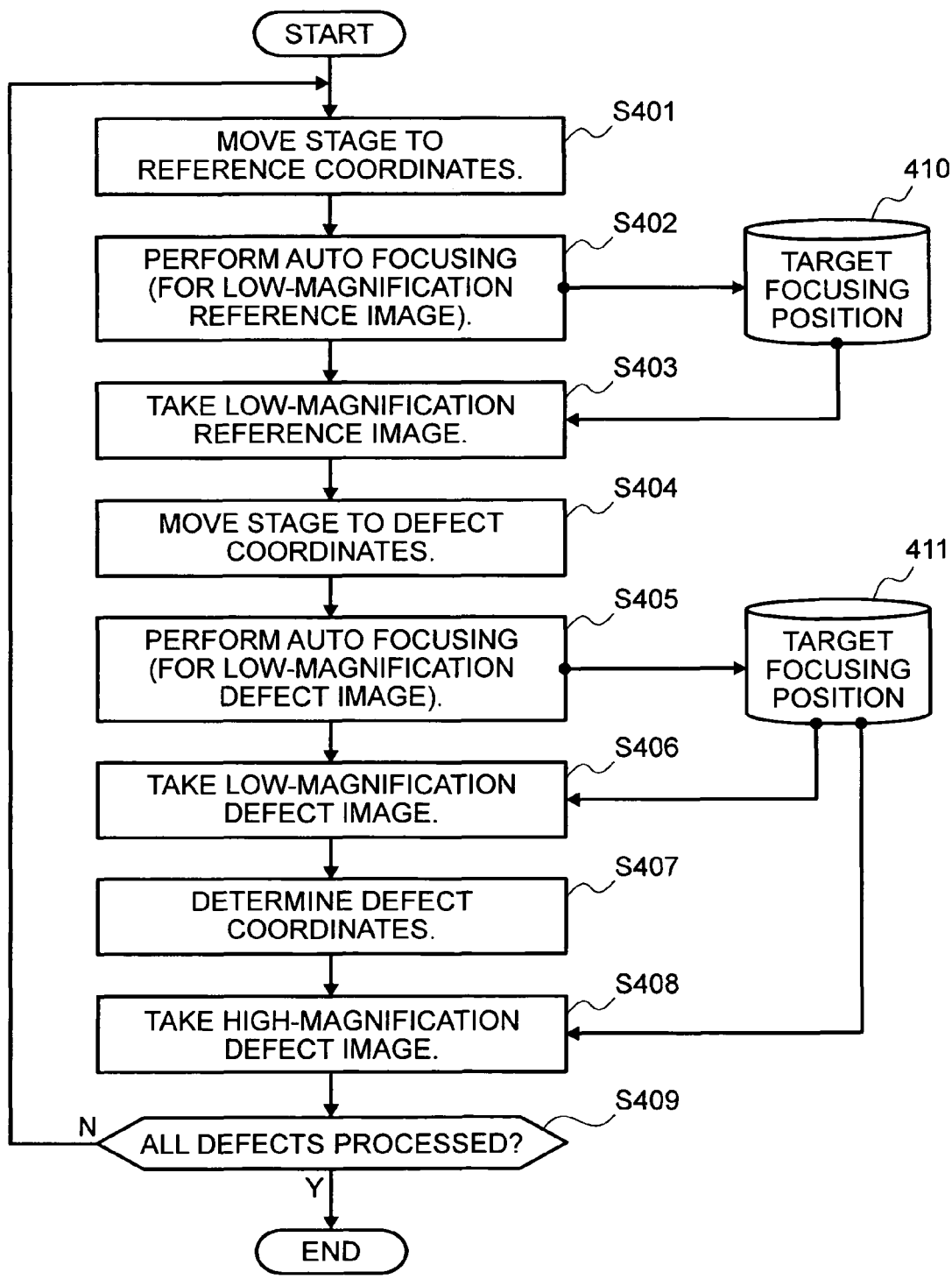
FIG. 4 is a flowchart of an ADR sequence according to a first embodiment of the invention.
Figure 5:
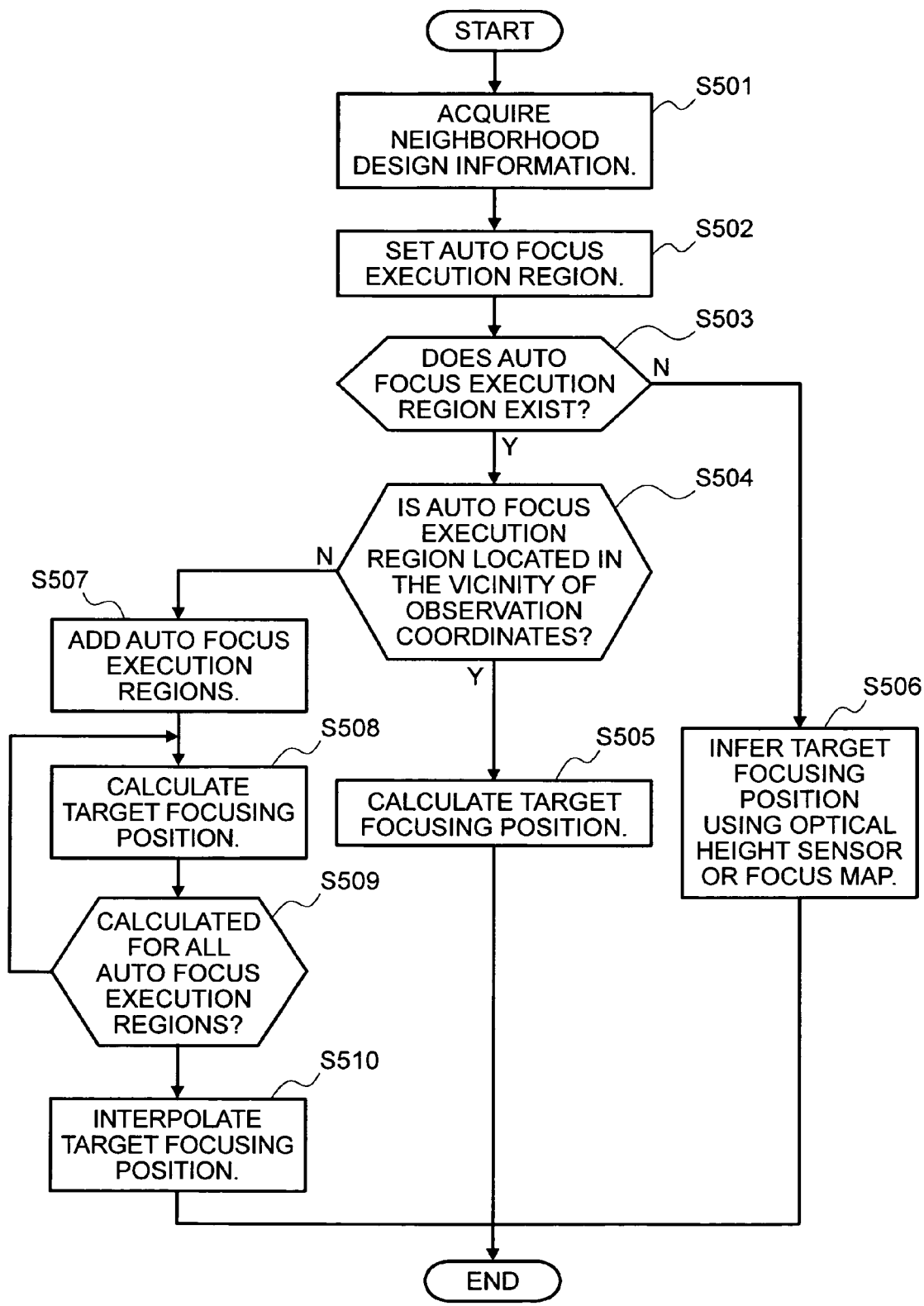
FIG. 5 is a flowchart of a sequence of SEM image auto focusing according to the first embodiment of the invention.

Although the example of FIGS. 4 and 5 is such that the auto focus execution region setting step S502 is executed in the auto focusing step S402 which is executed after the stage moving step S401, the auto focus execution region setting step S502 may be executed parallel with the stage moving step S401. Still another procedure is possible in which the auto focus execution region setting step S502 is executed before a start of observation and information of an auto focus execution region 610 is stored in the storage section 114 in advance. In this case, the auto focusing step S402 is made as simple as processing that the information of the auto focus execution region 610 that was generated in advance and is stored in the storage section 114 is read from the storage section 114 at a step corresponding to the auto focus execution region setting step S502.

Let V represent a positional difference between a low-magnification reference image and a low-magnification defect image; then, the auto focusing step S405 for a low-magnification defect image may use an auto focus execution region obtained by shifting, by V, an auto focus execution region that was set in the auto focusing step S402 for a low-magnification reference image. This is because the same patterns are formed in a defect image imaging region and a reference image imaging region except for a defect portion.

The information of the thus-set auto focus execution region (see FIG. 6(d), for example) is displayed on the screen of the input/output section 117, and is made adjustable by a user through the input/output section 117.

Returning to FIG. 5, the description of the auto focusing steps 402 and S405 will be continued. The auto focusing mode is switched on the basis of a manner of formation of wiring patterns which is obtained from at least one of the neighborhood design information and its image version.

First, if no auto focus execution region was set in the auto focus execution region setting step S502, since the reliability of SEM image auto focusing will be low, it is judged at a judgment step S503 that no auto focus execution region exists (step S503: N, that is, SEM image auto focusing is not executable). In this case, at step S506, a target focusing position is calculated by using an optical height sensor or a focus map obtained by performing interpolation on target focusing positions in a wafer surface. The calculation of a target focusing position using a focus map is disclosed in JP-A-2005-285746.

Figure 9:
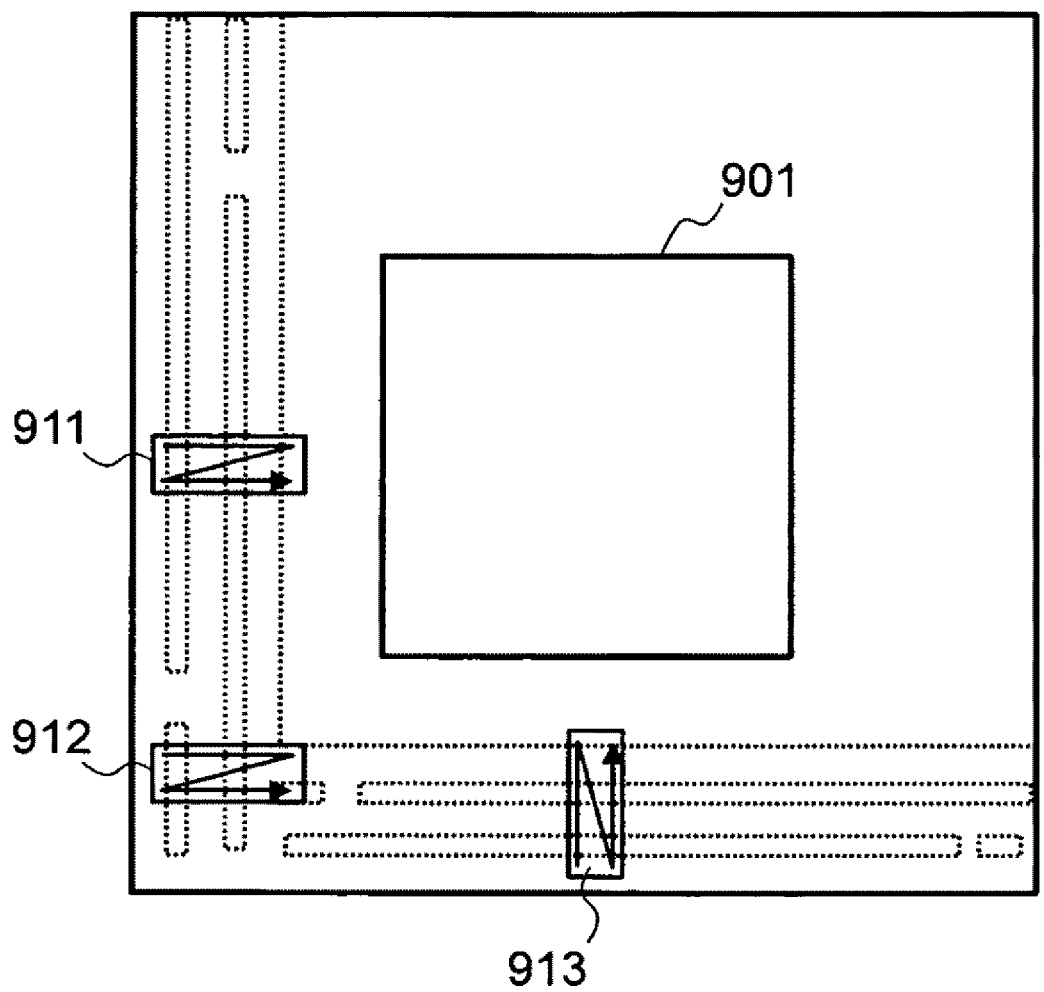
FIG. 9 shows an example of setting of an auto focus execution region according to the first embodiment of the invention.

On the other hand, if it is judged at step S503 that an auto focus execution region exists, then it is judged at step S504 whether the auto focus execution region is located in the vicinity of the observation coordinates. If it is judged that the auto focus execution region is not located in the low-magnification imaging region 901 or its the vicinity (S504: N; as in the case of FIG. 9), the distances between the imaging region (901 in FIG. 9) and regions where to determine a target focusing position (911, 912, and 913 in FIG. 9) are long and hence it may be impossible to correctly calculate target focusing positions in the imaging region. Therefore, at step S507 one or more auto focus execution region are set additionally in the vicinity of the low-magnification imaging region. At step S508 and S509, target focusing positions are calculated in the respective auto focus execution regions. At step S510, a target focusing position of the imaging region is determined by interpolating it between neighboring target focusing positions. The plural auto focus execution regions are set in respective edge-concentrated regions at coordinates positions having large values in a distance map 609. A simplest method for interpolating a target focusing position is to average the target focusing positions of respective regions. Where target focusing positions at three or more locations have been determined, interpolation may be performed by fitting a flat plane or a curved surface.

If it is judged that the auto focus execution region is located in the vicinity of the observation coordinates (S504: Y; as in the case of FIG. 6(d), for example), at step S505 a target focusing position is calculated by using the auto focus execution region 611 which is located inside or in the vicinity of the low-magnification imaging region 602.

Figure 8:
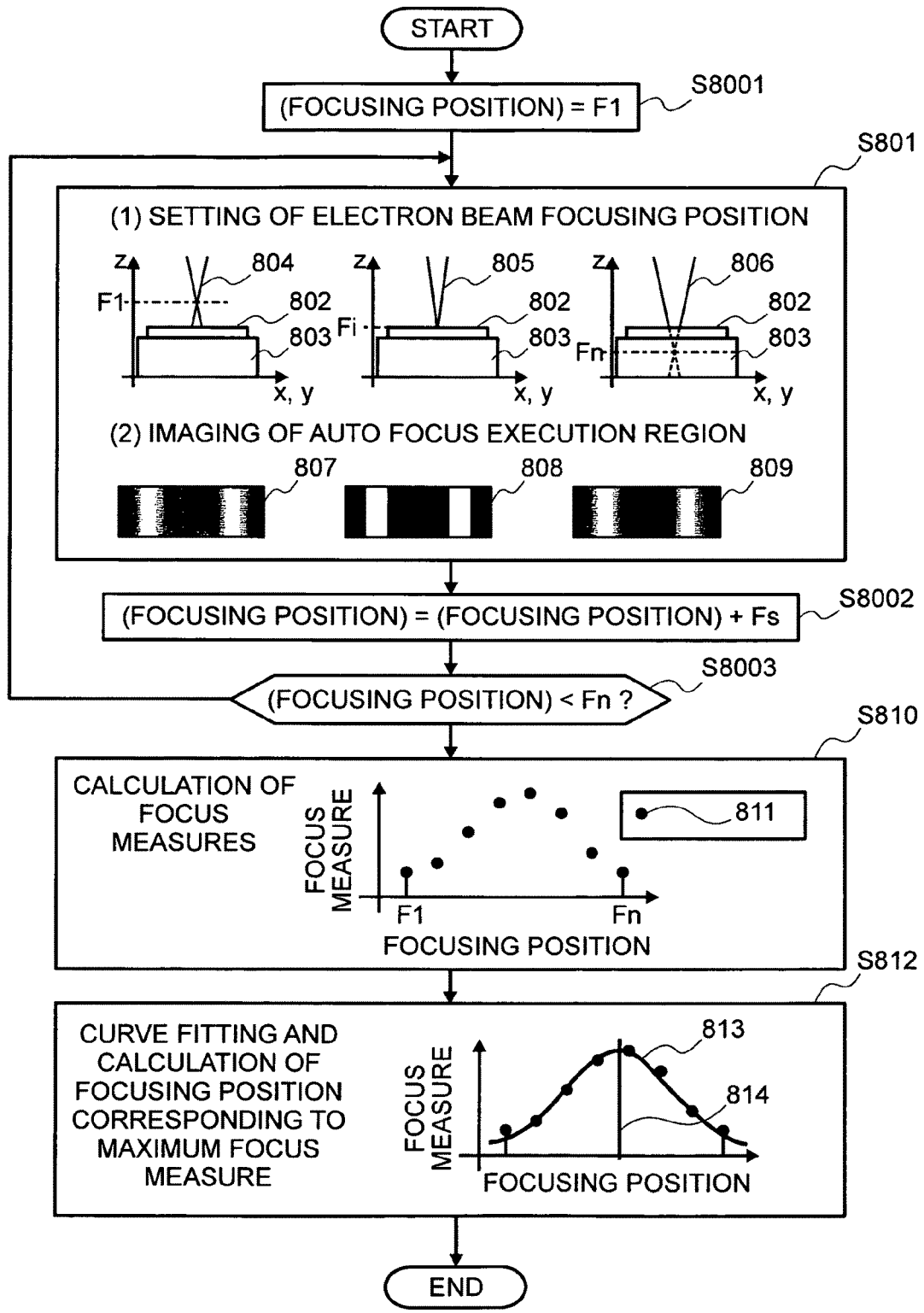
FIG. 8 shows an exemplary target focusing position calculating step according to the first embodiment of the invention.

The target focusing position calculating steps S505 and S508 will be described below with reference to FIG. 8. While the focusing position is varied from F1 to Fn, the set region is imaged and an image is acquired every time the focusing position is varied by Fs (S8001, S801, S8002, and S8003). Reference numeral 807 denotes an image that is taken in a state that the focusing position is set at F1 at step S8001. Reference numeral 809 denotes an image that is taken in a state that the focusing position is set at Fn as a result of repeated execution of steps S8002 and S8003. The images 807 and 809 are blurred because electron beams 804 and 806 are not focused on the surface of a wafer 802 that is held on a stage 803. Reference numeral 808 denotes an image that is taken in a state that the focusing position is set at Fi which is close to a target focusing position and an electron beam 805 is focused on the wafer surface. Edges are very sharp in the image 808.

At step S810, focus measures 811 are calculated from the respective acquired images. The focus measure is an index that indicates a degree of focusing and can be observed as edge sharpness in an image taken. Therefore, an edge extraction filter such as a Laplacian filter is applied to each acquired image and the sum or variance of density values of an output image is employed as a focus measure.

Focus measures calculated from the respective images are plotted with the focusing position as the horizontal axis, whereby a distribution that is convex upward and has a target focusing position at the center is obtained. Since this distribution is discrete, that is, the focusing positions are separated from each other by Fs, at step S812 interpolation is performed by fitting a Gaussian curve or quadratic curve 813 to the distribution and a focusing position 814 having a maximum value is employed as a target focusing position.

According to this embodiment, since a low-magnification reference image and a low-magnification defect image are acquired after an auto focus execution region is set, a target focusing position can be detected reliably and the time taken to acquire a low-magnification reference image and a low-magnification defect image can surely be made shorter than in conventional cases.

Furthermore, since a high-magnification defect image is taken by using information of auto focusing that was performed in taking a low-magnification defect image, unlike in conventional cases it is not necessary to perform auto focusing again in taking a high-magnification defect image, which makes it possible to shorten the ADR processing time.

Embodiment 2

Although the ADR sequence according to the first embodiment is such that a defect position in a low-magnification defect image is determined by using a low-magnification reference image and a low-magnification defect image, the invention can also be applied to a case as disclosed in JP-A-2003-98114 in which the ADR sequence is such that a defect position is determined without using a reference image by making use of the periodicity of patterns in an imaging region in a memory cell area. In this case, steps S401-S403 of the ADR sequence shown in FIG. 4 are not necessary and step S404 and the following steps are executed. The auto focusing as described in the first embodiment is performed at step S405.

The invention can also be applied to a case as disclosed in JP-A-2007-40910 in which the ADR sequence determines a defect position without using a reference image even in the case where an imaging region includes part of logic patterns that exist in a peripheral portion of a memory cell area. Also in this case, steps S401-S403 of the ADR sequence shown in FIG. 4 are not necessary and step S404 and the following steps are executed. The auto focusing as described in the first embodiment is performed at step S405.

Embodiment 3

In the first and second embodiments, the ADR sequence is such that a defect position is determined from a low-magnification image and the determined position is imaged at a high magnification. On the other hand, an ADR sequence is possible in which no low-magnification imaging is performed and high-magnification imaging is performed with a wide field of view. In this ADR sequence, a defect position is determined from an image of many pixels taken with a wide field of view and a defect image is generated by cutting out pixels that are centered by the determined defect position. When pixels are cut out, they may be deformed by image processing. At this time, a defect position is determined from the difference between a reference image and a defect image taken at a high magnification with a wide filed of view (see the first embodiment). Alternatively, a defect position may be determined from only a defect image (see the second embodiment).

In this ADR sequence, the invention can be applied to auto focusing that is performed before high-magnification imaging.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A method for observing defects using a scanning electron microscope, comprising the steps of:
    setting an imaging region on a specimen where to perform auto focusing a scanning electron microscope on the basis of design information of the specimen;
    imaging the thus-set imaging region on the specimen plural times at a first magnification while varying the focusing position of the scanning electron microscope in a direction perpendicular to the specimen;
    determining target focusing position information of the scanning electron microscope from plural image signals of the imaging region acquired by imaging the imaging region plural times at the first magnification while varying the focusing position;
    imaging the specimen at a second magnification which is lower than the first magnification with the scanning electron microscope using the determined target focusing position information;
    acquiring position information of a defect detected by an inspection apparatus from an image of the specimen acquired by imaging the specimen at the second magnification;
    imaging the specimen at a third magnification which is higher than the second magnification with the scanning electron microscope using the acquired position information of the defect and the determined target focusing position information; and
    extracting an image of the defect detected by the inspection apparatus from an image of the specimen acquired by imaging the specimen at the third magnification;
    wherein the step of setting the imaging region is performed to set a plurality of imaging regions where to perform auto focusing for each defect of the defects detected by the inspection apparatus;
    wherein the step of imaging the thus-set imaging region is performed to image each of the plurality of the imaging regions plural times at the first magnification; and
    wherein the step of determining target focusing position information is performed to determine by using plural image signals of the plurality of the imaging regions.

2. The method according to claim 1, wherein the imaging region on the specimen where to perform auto focusing for each defect of the defects detected by the inspection apparatus is set so as to include a region that is located in the vicinity of the position of the defect on the specimen and has pattern edges.

3. The method according to claim 1, wherein the imaging region on the specimen where to perform auto focusing for each defect of the defects detected by the inspection apparatus is set so as to include a region that is located in the vicinity of the position of the each defect on the specimen and in which wiring patterns are concentrated.

4. The method according to claim 2, wherein imaging the imaging region on the specimen with the scanning electron microscope is performed by scanning an electron beam of the scanning electron microscope in a direction that is perpendicular to the pattern edges of the specimen.

5. The method according to claim 1, wherein the imaging of the specimen at the second magnification with the scanning electron microscope using the target focusing position information includes imaging a first region including the each defect on the specimen using the position information of the defect detected by the inspection apparatus and imaging a second region where the each defect does not exist and the same patterns as in the first region should be formed.

6. A scanning electron microscope system for observing defects, comprising:
a scanning electron microscope for acquiring an image of an observation subject specimen by detecting secondary charged particles that are generated from the observation subject specimen by irradiating and scanning the observation subject specimen with a focused electron beam;
control means for controlling the scanning electron microscope;
first storing means for storing position information of defects on the observation subject specimen detected by a separate inspection apparatus;
second storing means for storing design information of the observation subject specimen;
image processing means for processing the image of the observation subject specimen acquired by the scanning electron microscope;
computing and storing means for calculating and storing a target focusing position for the observation subject specimen of the scanning electron microscope; and
input/output means connected to the control means, the first storing means, the second storing means, the image processing means, and the computing and storing means, for performing information input and output, wherein:
the control means sets a plurality of imaging regions on the observation subject specimen where to perform auto focusing the scanning electron microscope on the basis of position information of each defect of the defects on the observation subject specimen detected by the inspection apparatus and stored in the first storing means, and images the thus-set imaging regions on the observation subject specimen for each defect of the defects detected plural times at a first magnification by controlling the scanning electron microscope while varying the focusing position of the scanning electron microscope in a direction perpendicular to the specimen;
the computing and storing means calculates target focusing position information for the observation subject specimen of the scanning electron microscope from plural image signals of the imaging regions acquired by imaging the imaging regions plural times at the first magnification by controlling the scanning electron microscope while varying the focusing position;
the control means images the observation subject specimen at a second magnification which is lower than the first magnification by controlling the scanning electron microscope using the target focusing position information calculated by the computing and storing means;
the image processing means acquires position information, on the scanning electron microscope, for the each defect of the defects detected by the inspection apparatus by processing an image of the observation subject specimen acquired by imaging the observation subject specimen at the second magnification by controlling the scanning electron microscope with the control means, and images the observation subject specimen at a third magnification which is higher than the second magnification by controlling the scanning electron microscope using the position information of the each defect of the defects acquired by processing the image with the image processing means and the target focusing position information stored in the computing and storing means; and
the image processing means extracts an image of the defect detected by the inspection apparatus from an image of the observation subject specimen acquired by imaging the observation subject specimen at the third magnification by controlling the scanning electron microscope with the control means.

7. The system according to claim 6, wherein the control means sets imaging regions on the observation subject specimen where to perform auto focusing for the each defect of the defects detected so that it includes a region that is located in the vicinity of the position of the defect on the observation subject specimen and has pattern edges.

8. The system according to claim 6, wherein the control means sets the imaging regions on the observation subject specimen where to perform auto focusing for the each defect of the defects detected so that it includes a region that is located in the vicinity of the position of the defect on the observation subject specimen and in which wiring patterns are concentrated.

9. The system according to claim 7, wherein the control means controls the scanning electron microscope so as to scan the imaging regions on the observation subject specimen with the electron beam in a direction that is perpendicular to the pattern edges of the specimen.

10. The system according to claim 6, wherein the control means images the observation subject specimen at the second magnification with the scanning electron microscope using the target focusing position information by imaging a first region including the each defect of the defects detected on the specimen using the position information of the each defect of the defects detected by the inspection apparatus and imaging a second region where the each defect of the defects detected does not exist and the same patterns as in the first region should be formed.

11. A scanning electron microscope system for observing defects, comprising:
a scanning electron microscope for acquiring an image of an observation subject specimen by detecting secondary charged particles that are generated from the observation subject specimen by scanning the observation subject specimen with a focused electron beam;
design information storing means for storing design information of the observation subject specimen;
imaging region setting means for setting a plurality of imaging regions on the observation subject specimen where to perform auto focusing the scanning electron microscope on the basis of position information of each defect of the defects on the observation subject specimen detected by a separate inspection apparatus and the design information of the observation subject specimen stored in the design information storing means;
target focusing position calculating means for calculating target focusing position information of the scanning electron microscope from plural image signals acquired by imaging the imaging region set by the imaging region setting means for each defect of the defects detected plural times at a first magnification with the scanning electron microscope while varying the focusing position of the focused electron beam in a direction perpendicular to the specimen;
imaging control means for acquiring a magnification defect image and reference image by imaging, at a second magnification which is lower than the first magnification, a first region including the each defect on the observation subject specimen of the defects detected by the inspection apparatus using the target focusing position information calculated by the target focusing position calculating means and a second region where the each defect of the defects detected does not exist and the same patterns as in the first region should be formed;

defect position calculating means for determining defect position information for the each defect of the defects detected by comparing the magnification defect image and reference image acquired by controlling the scanning electron microscope with the imaging control means; and defect image acquiring means for acquiring an image of the each defect of the defects detected by imaging the each defect of the defects detected at a third magnification which is higher than the second magnification using the target focusing position information calculated by the target focusing position calculating means by controlling the scanning electron microscope on the basis of the defect position information determined by the defect position calculating means.

12. The system according to claim 11, wherein the imaging region setting means sets an imaging region on the observation subject specimen where to perform auto focusing for each defect of the defects detected so that it includes a region that is located in the vicinity of the position of the each defect of the defects detected on the observation subject specimen and has pattern edges.

13. The system according to claim 11, wherein the imaging region setting means sets an imaging region on the observation subject specimen where to perform auto focusing for each defect of the defects detected so that it includes a region that is located in the vicinity of the position of the each defect of the defects detected on the observation subject specimen and in which wiring patterns are concentrated.

14. The system according to claim 11, wherein the target focusing position calculating means calculates target focusing position information of the scanning electron microscope from plural image signals acquired by scanning the imaging region for each defect of the defects detected on the observation subject specimen set by the imaging region setting means with the electron beam of the scanning electron microscope in a direction that is perpendicular to pattern edges of the specimen included in the imaging region.

* * * * *